(12) United States Patent
Marino et al.

(10) Patent No.: US 11,992,229 B2
(45) Date of Patent: May 28, 2024

(54) METHODS, SYSTEMS, AND DEVICES FOR DIAGNOSING AND TREATING INTERVERTEBRAL DISC DEGENERATION

(71) Applicant: Trinity Orthopedics, LLC, San Diego, CA (US)

(72) Inventors: James F. Marino, La Jolla, CA (US); Dale Binke, San Diego, CA (US); Jamil Elbanna, San Diego, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 54 days.

(21) Appl. No.: 17/854,837

(22) Filed: Jun. 30, 2022

(65) Prior Publication Data

US 2022/0401114 A1 Dec. 22, 2022

Related U.S. Application Data

(63) Continuation of application No. 16/684,963, filed on Nov. 15, 2019, now Pat. No. 11,376,021, which is a
(Continued)

(51) Int. Cl.
*A61B 17/16* (2006.01)
*A61B 17/17* (2006.01)
*A61B 17/00* (2006.01)

(52) U.S. Cl.
CPC ...... *A61B 17/1671* (2013.01); *A61B 17/1633* (2013.01); *A61B 17/1757* (2013.01);
(Continued)

(58) Field of Classification Search
CPC ............ A61B 17/1671; A61B 17/1757; A61B 17/1631
See application file for complete search history.

(56) References Cited

U.S. PATENT DOCUMENTS 6,607,530 B1  8/2003  Carl et al.
8,021,401 B2  9/2011  Carl et al.
(Continued)

OTHER PUBLICATIONS

Adams, M.A., et al. "Abnormal stress concentrations in lumbar intervertebral discs following damage to the vertebral bodies: a cause of disc failure?" *European Spine Journal.* vol. 1, (1993) pp. 214-221.
(Continued)

*Primary Examiner* — Olivia C Chang
(74) *Attorney, Agent, or Firm* — Mintz Levin Cohn Ferris Glovsky and Popeo, P.C.

(57) ABSTRACT

A method of diagnosing, minimizing symptoms and/or treating the pathology of intervertebral disc degeneration includes introducing a first cannula through a vertebra along an axis of at least one pedicle of the vertebra from a generally posterior to a generally anterior direction and inserting a second cannula within a lumen of the first cannula, the second cannula constrained to a relatively straight configuration within at least a portion of the first cannula and assumes a nonlinear or curvilinear geometry external to the first cannula within at least a portion of a vertebral body of the vertebra and away from a longitudinal axis of the first cannula. The method includes forming a channel with the second cannula, the channel extending to or adjacent to a vertebral endplate of the vertebral body in order to create a defect through the vertebral endplate of the vertebra. Related systems, devices, and methods are described.

20 Claims, 7 Drawing Sheets

Related U.S. Application Data continuation of application No. 15/186,057, filed on Jun. 17, 2016, now Pat. No. 10,478,199.

(60) Provisional application No. 62/182,316, filed on Jun. 19, 2015.

(52) U.S. Cl.
CPC .............. *A61B 2017/00309* (2013.01); *A61B 2017/00323* (2013.01)

(56) References Cited

U.S. PATENT DOCUMENTS

| | | |
|---|---|---|
| 8,845,642 B2 | 9/2014 | Carl et al. |
| 9,393,127 B2 | 7/2016 | Carl et al. |
| 2003/0130664 A1 | 7/2003 | Boucher et al. |
| 2010/0114098 A1 | 5/2010 | Carl |
| 2010/0268237 A1 | 10/2010 | Carl et al. |
| 2012/0191094 A1 | 7/2012 | Alain et al. |
| 2014/0046245 A1 | 2/2014 | Cornacchia |

OTHER PUBLICATIONS

Chen, Hongmei, et. al. "Drilling and Microfracture Lead to Different Bon Structure and Necrosis during Bone-Marrow Stimulation for Cartilage Repair." *Journal of Orthopaedic Research*, vol. 27, (2009), pp. 1432-1438.

Holm, S., et al. "Nutrition of the Intervertebral Disc: Solute Transport and Metabolism." *Connective Tissue Research*, vol. 8, No. 2, (1981) pp. 101-119.

Holm, Sten, et al. "Experimental Disc Degeneration Due to Endplate Injury." *Journal of Spinal Disorders and Techniques*, vol. 17, No. 1, (2004), pp. 64-71.

Latridis, James C. and Andrew C. Hecht. "Commentary: Does needle injection cause disc degeneration? News in the continuing debate regarding pathophysiology associated with intradiscal injections." *The Spine Journal*, vol. 12, (2012), pp. 336-338.

Marchand, Catherine, et al. "Microdrilled Cartilage Defects Treated with Thrombin-Solidified Chitosan/Blood Implant Regenerate a More Hyaline, Stable, and Structurally Integrated Osteochondral Unit Compared to Drilled Controls." *Tissue Engineering: Part A*, vol. 18, No. 5-6, (2012), pp. 508-519.

Urban, Jill P.G., et al. "Nutrition of the Intervertebral Disc." *Spine*, vol. 29, No. 23, (2004), pp. 2700-2709.

Vadala, Gianluca, et al. "The Transpedicular Approach As an Alternative Route for Intervertebral Disc Regeneration." *Spine* vol. 38, No. 6, (2013), pp. E319-E324.

U.S. Appl. No. 16/757,357, filed Apr. 17, 2020, 20200237336.

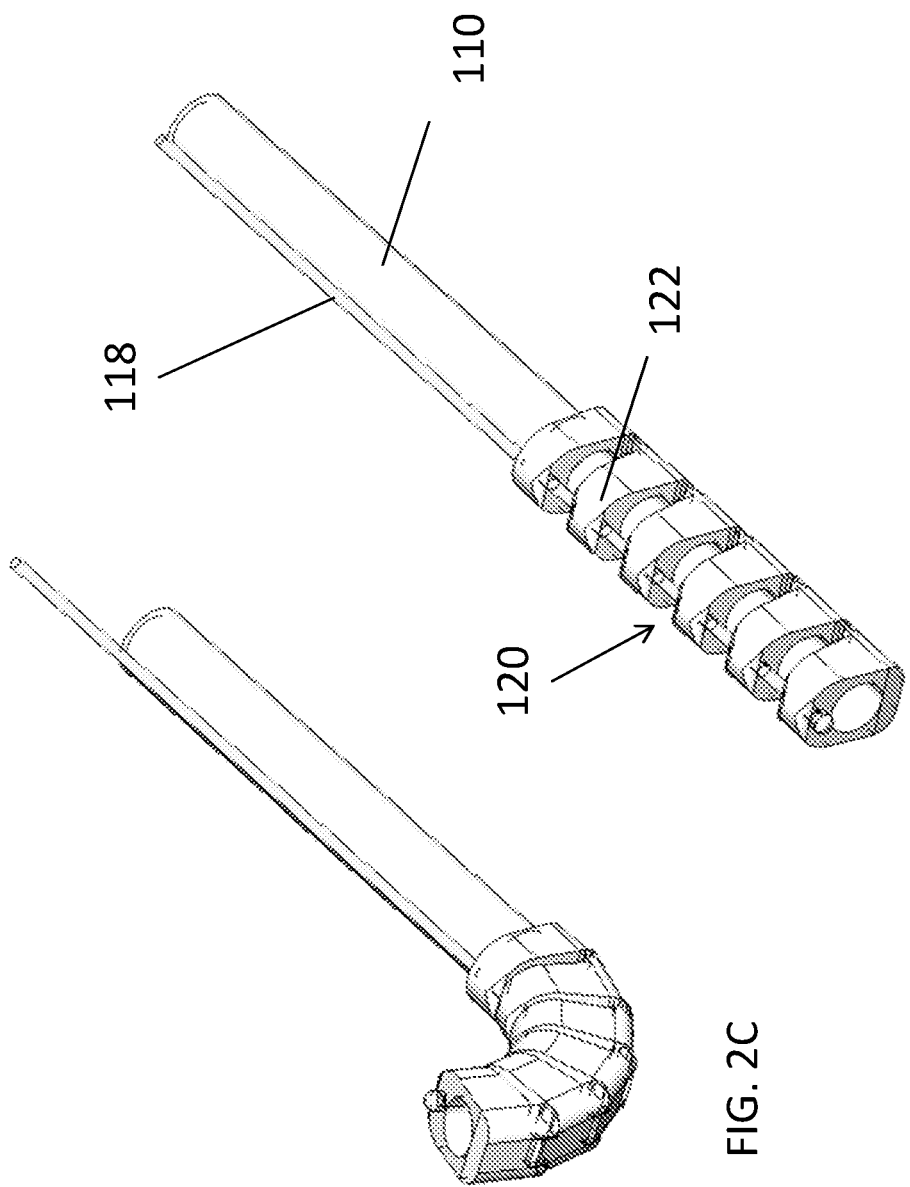

METHODS, SYSTEMS, AND DEVICES FOR DIAGNOSING AND TREATING INTERVERTEBRAL DISC DEGENERATION

CROSS-REFERENCE TO PRIORITY DOCUMENT

This application is a continuation of U.S. patent application Ser. No. 16/684,963, filed on Nov. 15, 2019, issuing on Jul. 5, 2022 under U.S. patent Ser. No. 11/376,021, which is a continuation of U.S. patent application Ser. No. 15/186,057, filed Jun. 17, 2016, now U.S. patent Ser. No. 10/478,199, which claims priority under 35 U.S.C. § 119(e) U.S. Provisional Patent application Ser. No. 62/182,316, filed Jun. 19, 2015, and entitled "Methods, Systems, and Devices for Diagnosing and Treating Intervertebral Disc Degeneration," which are incorporated by reference herein in their entireties.

BACKGROUND

Degeneration of the intervertebral disc is normally associated with the aging process. In some individuals disc degeneration can be precipitated by recognized disc trauma (e.g. repetitive heavy loading of the disc or an isolated disc injury) or may be a consequence of an apparently heritable condition (i.e. "juvenile disc degeneration"). Disc degeneration can involve anatomical (micro and macro anatomic) as well as biochemical alterations of the disc and tissues adjacent the disc such as the annulus and vertebral endplate. For example, disc desiccation and vertebral endplate sclerosis are intervertebral changes that can occur. Excessive loading (either singly or repetitive) can result in increased vertebral endplate ossification (i.e. increased bone formation) of the normally porous, but condensed cancellous bone. This ossification is theorized to reduce the normal diffusion of metabolites and catabolites to and from the highly vascularized vertebral body to and from the fibrocartilaginous disc space.

Degeneration can occur in a relatively asymptomatic manner or non-debilitating manner. In others, the process of disc degeneration can produce varying degrees of discomfort and disability. In the more debilitating forms of the disc degeneration, patients often seek interventions that can range from activity restrictions, NSAID treatment, and exercise therapy, to surgical management such as partial disc excision, disc resection and interbody arthrodesis (intervertebral fusion), or prosthetic disc replacement (arthroplasty).

Very few medical interventions are effective in fundamentally altering the underlying anatomic, pathophysiologic and/or biochemical changes that accompany intervertebral disc degeneration.

SUMMARY

In one aspect, disclosed is a method of diagnosing, minimizing a symptom and/or treating a pathology of intervertebral disc degeneration includes introducing a first cannula through a vertebra along an axis of at least one pedicle of the vertebra from a generally posterior to a generally anterior direction. The method includes inserting a second cannula within a lumen of the first cannula. The second cannula is constrained to a relatively straight configuration within at least a portion of the first cannula and the second cannula assumes a nonlinear or curvilinear geometry external to the first cannula within at least a portion of a vertebral body of the vertebra and away from a longitudinal axis of the first cannula. The method includes forming a channel with the second cannula, the channel extending to or adjacent to a vertebral endplate of the vertebral body in order to create a defect through the vertebral endplate of the vertebra.

The method can further include rotating the second cannula along the pedicle axis to alter a plane within which the second cannula resides to effect a different medial-lateral position for approaching and contacting the vertebral endplate to create at least a second defect through the vertebral endplate of the vertebra. The method can further include contacting the vertebral endplate at a plurality of locations with the second cannula to create a plurality of defects through the vertebral endplate of the vertebra. Contacting the vertebral endplate at the plurality of locations can occur as a result of one or more of employing both pedicles of the vertebra, employing the superior and inferior vertebrae, actuating the second cannula into different radial curvatures, and deploying the first cannula and/or the second cannula to various depths within the vertebra.

The second cannula can include a pliable, distal end region coupled to a steerable feature configured to tension the distal end region to deflect away from the longitudinal axis of the first cannula. The first cannula can be placed over a guide pin positioned within the at least one pedicle of the vertebra. The distal end region can deflect to take on a curvilinear shape. The pliable distal end region can include one or more slits forming a plurality of movable segments. The steerable feature can include a cable or wire coupled to the plurality of movable segments that is actuatable by a user. The second cannula can be fabricated from a superelastic metal.

The method can further include advancing a tool through an inner lumen of the second cannula. The tool can have a flexible, non-linear shaft and a distal tip. The distal tip of the tool can be configured to form the channel from the vertebral body through the vertebral endplate. The distal tip of the tool can be a micro-fenestrating trocar tip, a drill, or a burr drill.

The method can further include advancing a catheter through the second cannula. The catheter can be configured to deliver a diagnostic tool and/or a therapeutic agent. The diagnostic tool can be an intradiscal pressure transducer for discomanometry.

The defect in the vertebral endplate can stimulate bleeding and recruitment of cellular and humoral inflammatory cytokine production adjacent the defect. Neovascularization and fibrocartilaginous formation can be induced along the channel and the defect. The method can lessen the feeling of pain in the patient. The defect can have a diameter of between 0.25 mm and 3 mm.

In some variations, one or more of the following can optionally be included in any feasible combination in the above methods, apparatus, devices, and systems. More details of the devices, systems, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIG. 2B-2C are perspective views of an implementation of the curvilinear cannula extending in a straight and curved configuration, respectively;

Figure 1A:
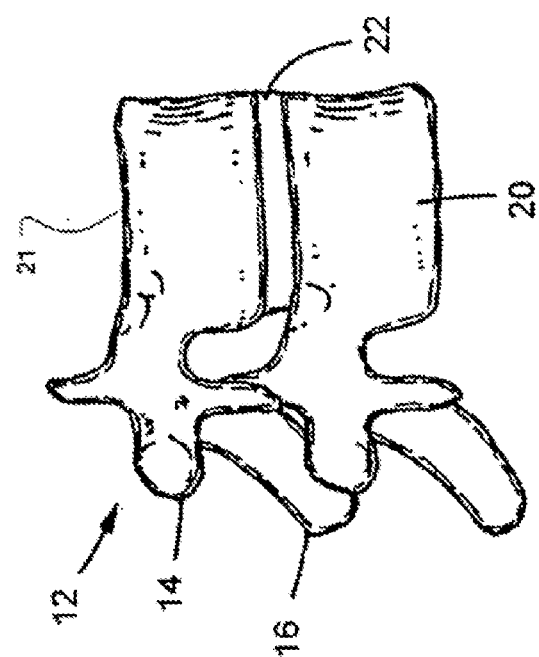
FIG. 1A is a simplified sagittal view of a pair of vertebrae.
Figure 1B:
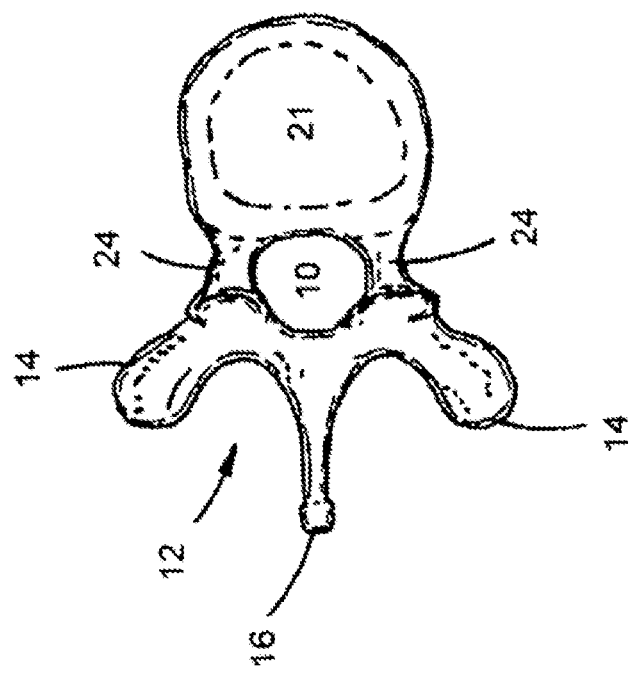
FIG. 1B is a simplified, sectional coronal view of the vertebrae shown in FIG. 1A.

It should be appreciated that the drawings herein are exemplary only and are not meant to be to scale. It is to be understood that devices described herein may include features not necessarily depicted in each figure.

DETAILED DESCRIPTION

The intervertebral disc (the largest avascular structure of the body) is nourished via a diffusion process of nutrients and metabolites from the adjacent "porous" vertebral endplates. Increased vertebral ossification can reduce the normal diffusion of metabolites and catabolites from and to the highly vascularized vertebral body to and from the fibro-cartilaginous disc space. Intervertebral nuclear metabolism is primarily anaerobic and occurs at very low oxygen tensions. Steep concentration gradients of metabolites such as oxygen, glucose, and lactic acid across the disc are present. Oxygen and glucose concentrations are the lowest in the center of the nucleus where lactic acid concentrations are the greatest. If the endplate calcifies or nutritional demand increases, the diffusive transport and actual levels of concentration can fall to critical levels. Cell death can occur upon loss of nutrient supply as well as loss of matrix production and increase in matrix degradation, which all lead to disc degeneration. Nutrient flow to the disc can also be disrupted due to repeated microfractures of the vertebrae and scarring of the endplate.

Relatively large surgically-induced defects in the endplate results in degradation of the adjacent intervertebral disc. Annular piercing and intradiscal injection of diagnostic agents associated with provocative diagnostic discography, and transient elevated intradiscal pressure from the injection can have a potential deleterious effect on the disc and are associated with subsequent accelerated disc degeneration.

Thus, the intervertebral disc has a nutritional dependence upon diffusion from micro-capillaries located in the porous structure of the endplates. The diffusion is dependent and proportional to the porosity and physiologic deformation of the endplate. Micro-anatomic changes, including endplate fractures (e.g. stress fractures due to repetitive loading and acute high loading), intra-vertebral disc herniations (i.e. Schmorl's nodes), reactive mineralization and scarring (i.e. endplate sclerosis), and micro-vascular degradative changes (e.g. diabetic basement membrane disease) can all contribute to diminished nutrition of the disc space and thus, diminished capacity for normal cellular viability and extracellular matrix maintenance.

Articular cartilage defects can be treated with various subchondral plate drill-hole fractures. The type of reparative tissue is affected by the size of the articular defect. Drill holes of 2 mm or less produce more hyaline cartilage (type II collagen fibers) than drill-hole defects greater than 2 mm, which tend to produce fibrous reparative cartilage (type I collagen fibers). Further, microdrilled cartilage defects having a diameter of 0.5 mm has less hyaline cartilage and collagen type II fibers than those of 0.9 mm diameter. Further, microdrilling produces better conditions for defect healing than microfracturing. Microdrilling has less hole sealing and more viable osteocytes compared to microfracturing. Further, deeper drilling from the articular surface into the bone produces a more robust subchondral hematoma response.

A linear transpedicular approach to the disc via the caudal pedicle for these diagnostic techniques does not go through the central axis of the pedicle. Such an approach is limited in its clinical utility due to the demands of "off-axis" trajectory as well as the obstructive limitations imposed by the iliac crest in the lower lumbar region. Further, this type of approach is limited in its intradiscal targeting.

The present disclosure relates to methods and devices for diagnosing and also treating intervertebral disc degeneration. Provided are improved methods and devices for performing diagnostic discography, discomanometry, and quantitative discomanometry that avoid issues of post annulus fibrosis needle puncture degeneration of the intervertebral disc. More particularly, provided are improved methods and devices for a non-linear pedicle approach coursing, in part, and generally along the pedicle central axis to perform discography, discomanometry, and quantitative discomanometry. Also provided herein are methods and devices for increasing diffusion of metabolites and catabolites to and from the vertebral body and disc space. Each will be described in more detail below.

Anatomy

As used herein, the terms "anterior" or "anteriorly" generally means from the front side or in the direction of the abdomen and "posterior" or "posteriorly" generally means from the backside or in the direction of the backside. "Cephalad," "superior," and "upper" generally mean towards a patient's head and "caudal," "inferior," and "lower" generally mean away from a patient's head. "Proximal" as used herein generally means nearer to a surgeon's point of reference and "distal" generally means further away from the surgeon's point of reference.

FIG. 1A is a simplified sagittal view of a pair of vertebrae and FIG. TB is a simplified, sectional coronal view of the vertebrae shown in FIG. TA. Each vertebrae include a vertebral 20, 21 having lamina 12, transverse processes 14, a spinous process 16, central canal 10, and pedicles 24. An intervertebral disc 22 having an outer annulus and an inner nucleus (not visible) is located between the endplates of the vertebral bodies 20, 21. The vertebral endplates are the top and bottom portions of the vertebral bodies that interface with the vertebral disc 22.

Figure 2A:
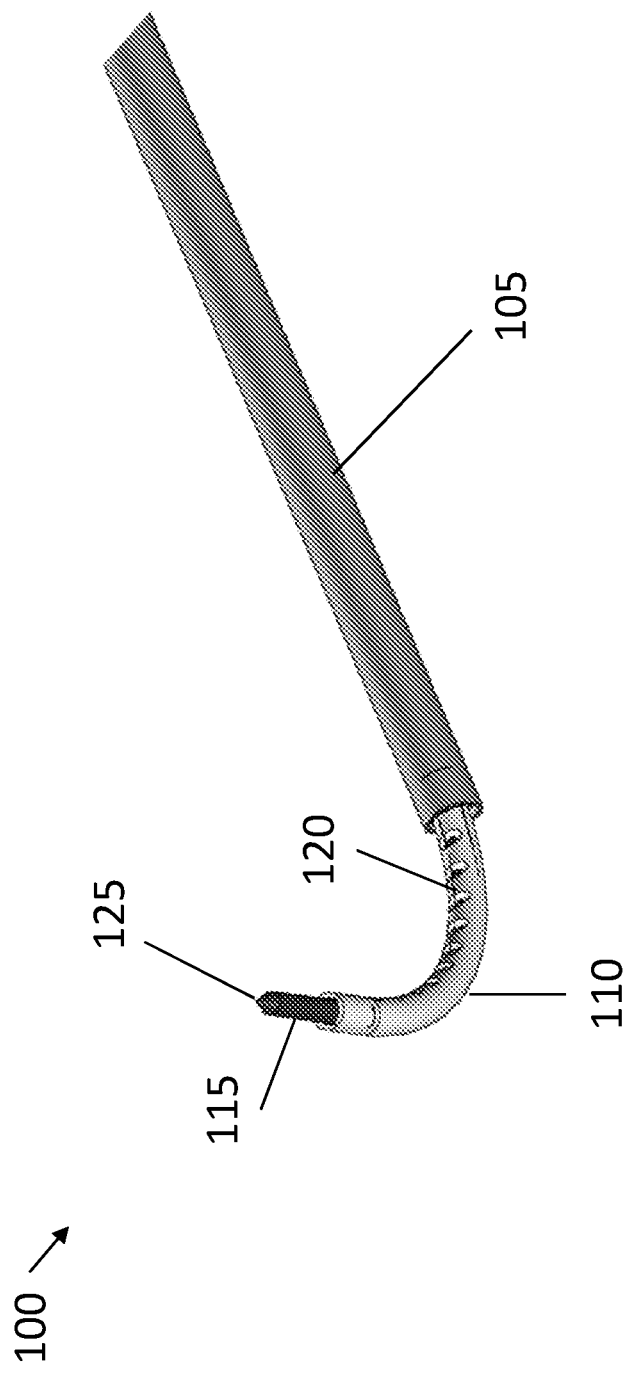
FIG. 2A is a perspective view of an implementation of a system for treating and/or diagnosing intervertebral disc degeneration.
Figure 3:
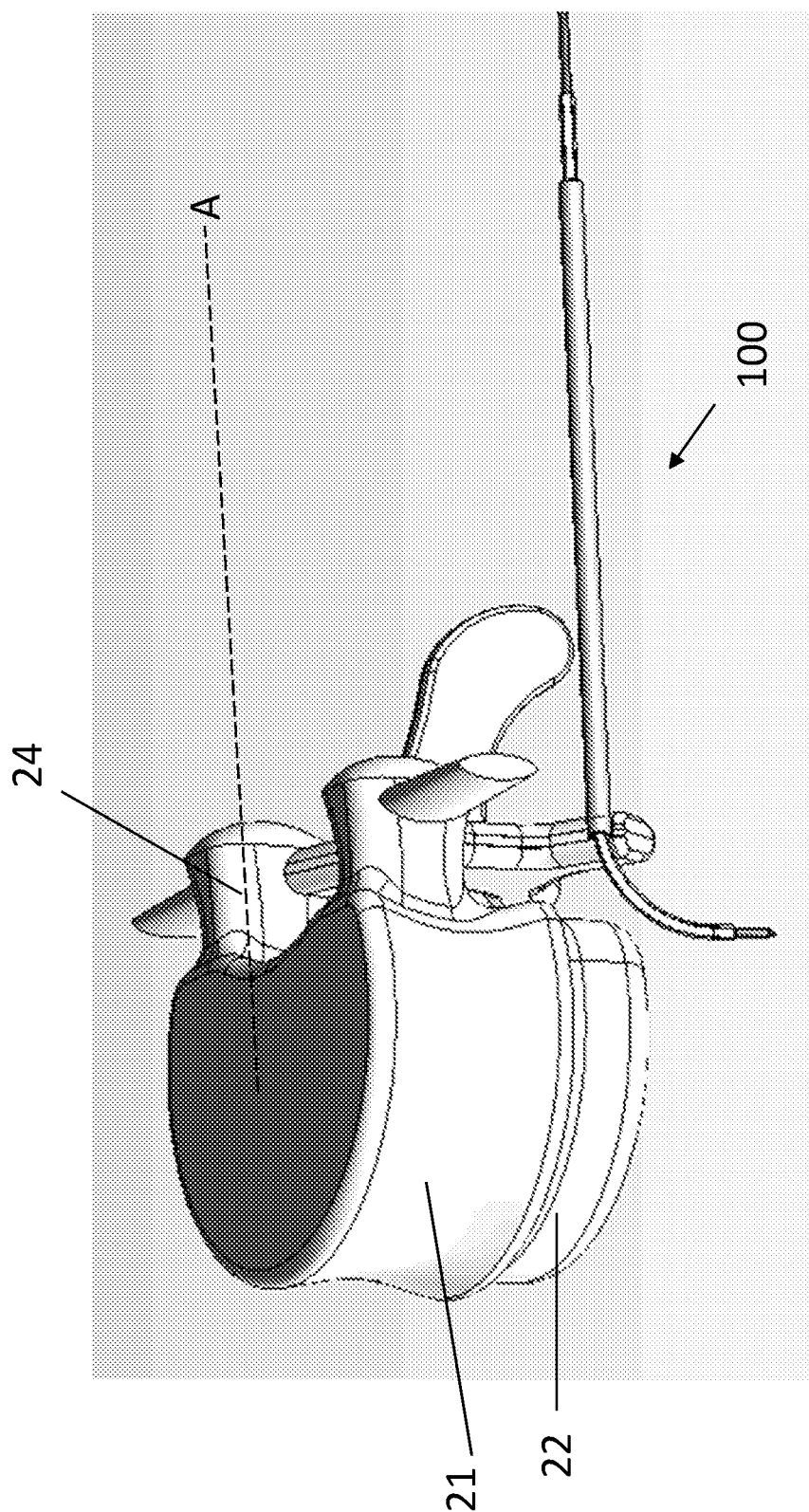
FIG. 3 is a perspective view of the system of FIG. 2A alongside a vertebra and intervertebral disc.

FIG. 2A illustrates an implementation of a system 100 configured to perform diagnostic and/or therapeutic techniques on an intervertebral disc 22 as will be described in more detail below. The system 100 can include a pedicle transport cannula 105 and a pliable curvilinear cannula 110. The pedicle transport cannula 105 can be generally elongate and straight. The pedicle transport cannula 105 can have an inner lumen such that it can be inserted over a guide pin (not shown), for example a guide pin positioned through the pedicle 24 along the pedicle axis A (see FIG. 3) in a posterior to anterior direction as will be described in more detail below.

The curvilinear cannula 110 can be fabricated from a pliable material or materials such as a superelastic metal (e.g. Nitinol). As shown in FIGS. 2B-2C, the curvilinear cannula 110 can have a steerable feature 118 near its distal end region. The steerable feature 118 can include a cable, wire, or other element associated with the pliable curvilinear cannula 110 capable of tensioning the cannula 110 to take on a different shape upon actuation. Additionally or alternatively, one or more stress relieving slits 120 can be incorporated in the curvilinear cannula 110 forming a plurality of segments 122 that are movable to increase the deformability of the curvilinear cannula 110. In some implementations, the slits 120 can be laser machined to create partial radial interruptions in the wall of the cannula 110 to form the segments 122. The feature 118 can be pulled proximally such that the distal end of the cannula deflects away from a longitudinal axis of the cannula 110 as the segments 122 compress together. The distal end of the cannula 110 can take on a curvilinear shape away from the longitudinal axis such that the radial interruptions narrow and the segments 122 approach one another. The relative size of the slits 120 can impact the degree of the shape change of the distal end of the cannula 110. Larger radial interruptions between the segments 122 can result in a sharper angle achieved at the distal end of the cannula.

Diagnostics

As described above, needle puncture injuries of the disc annulus during diagnostic discography, discomanometry, and quantitative discomanometry can contribute to annulus fibrosis and the degeneration of the intervertebral disc. The methods and devices for performing diagnostic discography, discomanometry, and quantitative discomanometry described herein minimize annular fibrosis and disc degeneration by using a non-linear pedicle approach coursing, in part, and generally along the pedicle central axis A.

Figure 4:
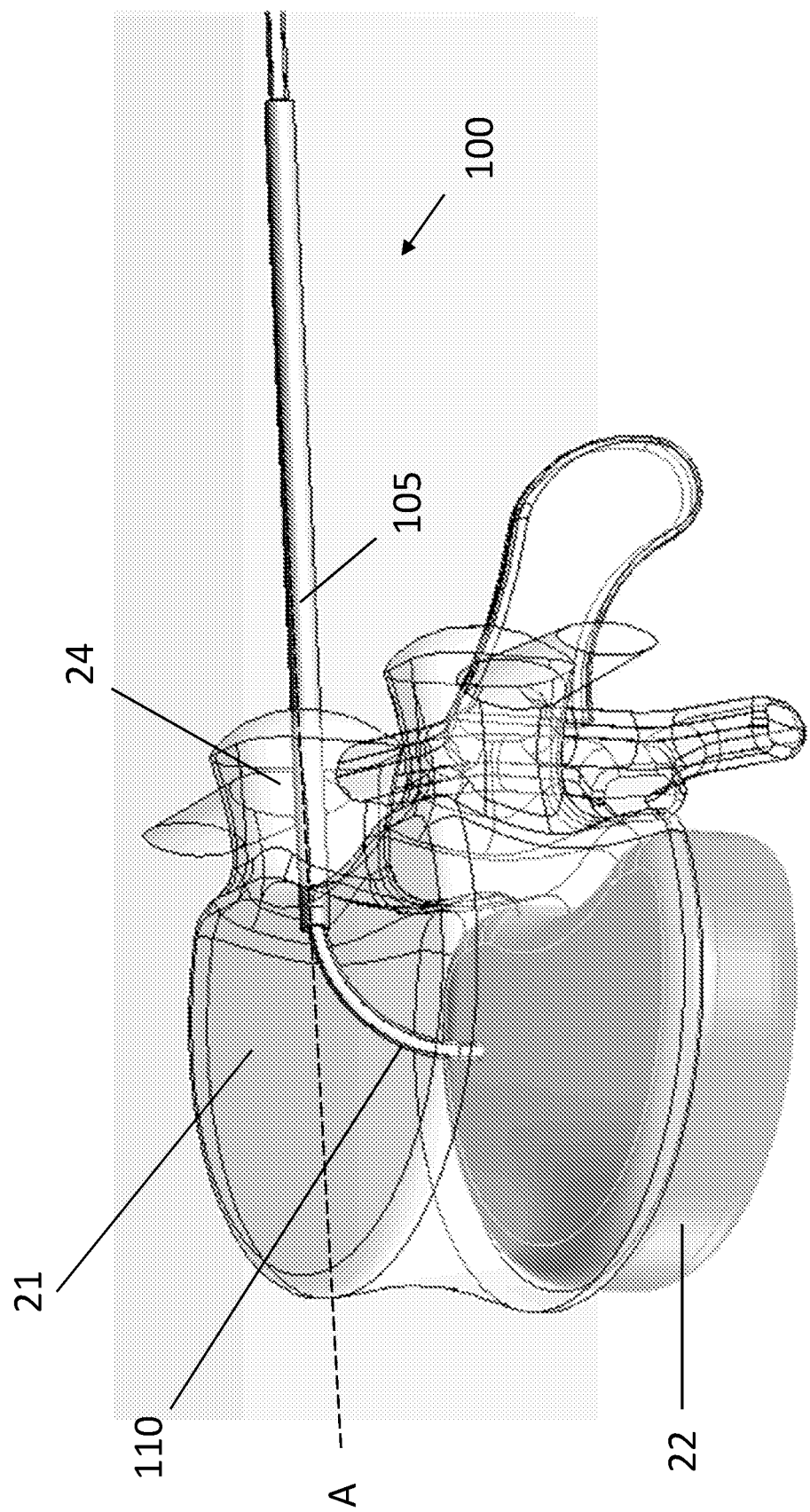
FIG. 4 is a perspective view of the system of FIG. 2A in use within the vertebra.
Figure 5:
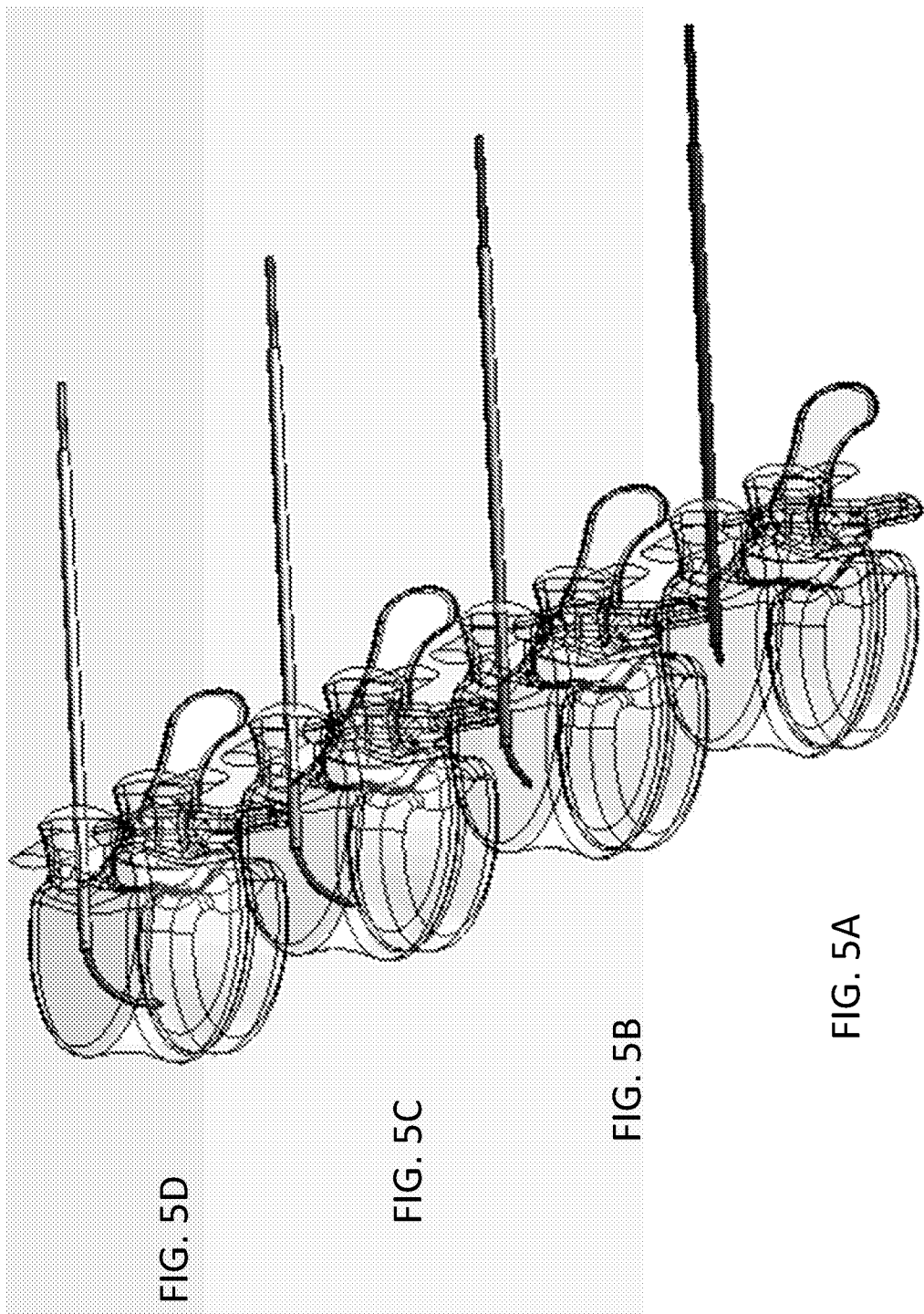
FIGS. 5A-5D are perspective views of the system of FIG. 2A in use within the vertebra.

In an implementation, the diagnostic device(s) can be placed percutaneously with the use of conventional pedicle screw targeting techniques such as fluoroscopy or other navigation methods. A guide pin can be placed within the pedicle 24 of a superior vertebra 21 along the pedicle axis A from posterior to anterior. After placing the guide pin generally along the pedicle axis A, the pedicle transport cannula 105 can be advanced over the guide pin. Alternatively, the transport cannula 105 with associated internal obturator can be exchanged for the initial guide pin. The transport cannula 105 with the internal obturator can be positioned along pedicle axis A in varying depths of anterior intravertebral positioning, such that the curvilinear cannula 110 upon exiting from the distal and anterior aspect of the pedicle transport cannula 105 can approach and contact the endplate at various corresponding posterior-anterior locations (see FIG. 4). Rotating the curvilinear cannula 110 along the general axis of the pedicle axis A to alter the plane within which the curvilinear cannula 110 resides can be used to effect different medial lateral positions for approaching and contacting the vertebral endplate. The methods described herein can be employed via one or both pedicles and in either the associated cephalad 21 and/or caudal 20 vertebra, as well as rotating the curvilinear cannula 110 and/or using curvilinear cannulas 110 with either a variable radius of curvature or of differing radial curvatures, and/or placing the transport cannula 105 along the pedicle axis A to different depths prior to deploying the curvilinear cannula(s) 110. A surgeon can effectively manipulate the distal operative end of the curvilinear cannula 110 to approach or contact the vertebral endplate in almost any location desired.

Again with respect to FIG. 2A, the system 100 can also include a tool 115 configured to be inserted through an inner lumen of the curvilinear cannula 110. The tool 115 can include a non-linear shaft that can include a distal tip 125. The distal tip 125 can be a micro-fenestrating trocar tip, drill, burr drill, or the like. The distal tip 125 can be advanced to and through the endplate and optionally into the intervertebral disc space (see FIGS. 5A-5D). A catheter can also be advanced through the curvilinear cannula 110 and used to deliver one or more diagnostic tools, including but not limited to agents such as radio-dense material for discography, a pressure transducer(s) for discomanometry, and other diagnostic tools or agents. It should be appreciated that therapeutic material can be delivered through the catheter as well.

In some implementations, such as for an indwelling device, the pedicle transport cannula 105 or an alternative indwelling catheter (such as a polymer catheter) placed using the methods described herein can be secured in place by a variety of mechanisms, including but not limited to, affixing the catheter or cannula to the pedicle transport cannula 105 or to a pedicle screw, via a threaded collar and circumferentially constricting collet, or by using a crimping sleeve, or via an interference friction lock, etc. The pedicle transport cannula may have an external thread form or other way to mitigate migration within the pedicle axis A. The curvilinear cannula 110 can be secured as well such as to the pedicle transport cannula 105. In some implementations of an indwelling discomanometric device, an intradiscal transducer can be connected by tubing and/or wiring to an implanted microprocessor for telemetric communication with an extracorporeal receiver and processor.

The non-linear transpedicular approach to the disc space using the methods, systems and devices described herein can also be useful as a diagnostic tool in evaluating changes in endplate compliance and/or micro-porosity. The devices, systems and methods described above can be used to simultaneously measure and compare the intradiscal pressure and the vertebral intraosseous pressure. Alternatively, a measurement of the local pressure immediately within or adjacent to a micro-fenestration or small defect in the endplate can be measured as an isolated value or in combination with other pressure data acquired (e.g. vertebral body pressure, venous pressure, arterial pressure, etc.). Volume pressure values (i.e. quantitative vertebral manometry) can be similarly acquired using the devices and methods described above.

The percutaneous transpedicular functional intervertebral intraosseous and/or intradiscal manometry can be used as a diagnostic allowing for determining disc and/or vertebral endplate changes associated with various pathologic and symptomatic states. For example, endplate sclerosis or increased bone density of the endplate associated with acute or repetitive trauma can result in reduced endplate compliance and reduced correlation of intradiscal pressures with vertebral intraosseous pressure.

Therapeutics

Figure 6:
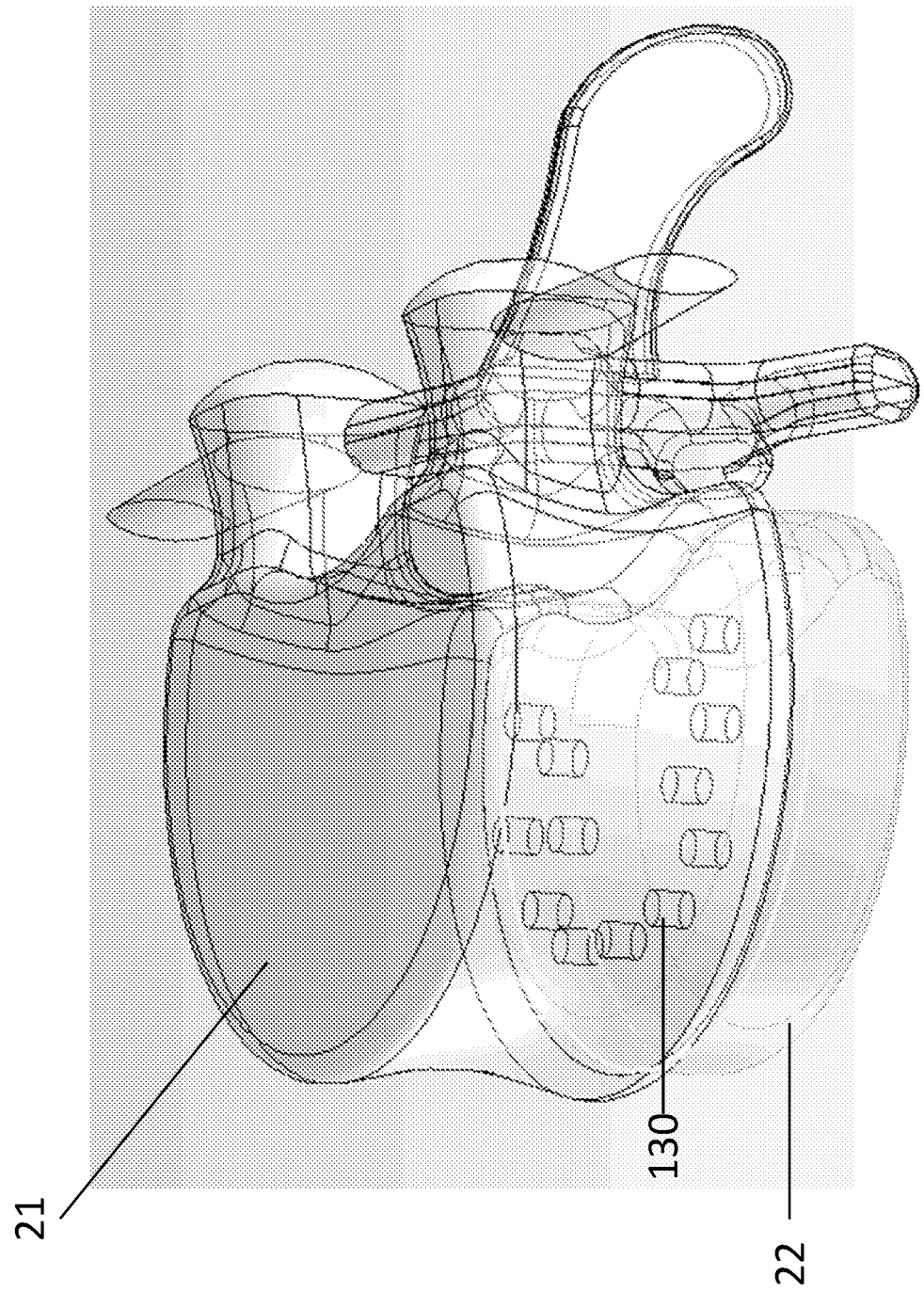
FIG. 6 is a perspective view of a vertebra having defects created within its endplate.

Also provided herein are methods and devices for creating small micro-fenestrations, channels, or defects 130 extending from the vertebral body through the endplate and into the intervertebral disc space to encourage an inflammatory healing cascade (see FIG. 6). The small channels or microfractures 130 in the endplate can stimulate initial bleeding followed by recruitment of cellular and humoral inflammatory cytokines in order to stimulate neovascularization and ultimately fibrocartilaginous formation along the path of the micro-drilling or micro-fracturing channel. This can enhance metabolite/catabolite diffusion from the vertebral body to and from the intervertebral disc space leading to improved disc physiology (e.g. fibrocartilaginous proliferation and repair) and ultimately reduced pain. Creation of defects 130 can also be used to relieve intraosseous pressure engorgement syndrome to allow for improved nutrient and catabolite diffusion to the disc space and/or reduce pathologically elevated intraosseous (perivertebral endplate) vertebral pressure. Additionally or alternatively, the defects 130 can reduce degenerative disc symptomology, for example, through an alteration of loading of associated nociceptive structures associated with the intervertebral disc and adjacent vertebrae motion segments.

In some implementations, the defects 130 can be less than 3 mm in diameter, less than 2 mm in diameter, less than 1.5 mm in diameter, less than 1 mm in diameter, less than 0.5 mm in diameter, less than 0.25 mm in diameter, less than 0.10 mm in diameter. In some implementations, the defects 130 can be between 0.25 mm and 3 mm in diameter. In some implementations, the defects 130 can be between 1.5 mm and 3 mm in diameter. The defects 130 can include multiple drill holes, trocar punches, micro-fractures, or micro-fenestrations distributed in either or both of the adjacent vertebral endplates associated with a symptomatic degenerative disc. The defects 130 can extend from the vertebral body through the endplate and into the intervertebral disc space, or potentially on through the disc and through the adjacent vertebral endplate. Any of a variety of drills or punch guides can be used to create the defects 130. The defects 130 can have any of a variety of geometric shapes and can be positioned through the endplates in any of a variety of patterns and/or locations.

The defects 130 can be performed by a variety of bone penetrating tools and methods, including pick micro-fracturing or micro-drilling using fluted drills, burrs, or laser energy, in a percutaneous manner. In some implementations, the defects 130 can be formed percutaneously using the nonlinear instrumentation described above. Again with respect to FIGS. 5A-5D, the curvilinear cannula 110 can be implanted and a tool 115 such as a drill or micro-pick shaft advanced through the linear pedicle transport cannula 105 to the vertebral body 21 to various anterior depths and in combination with various rotational orientations relative to the pedicle axis A to create one or more defects 130 (shown in FIG. 6) in the vertebral endplate of the vertebral body 21 into the intervertebral disc space 22. The method can be performed under fluoroscopic or spatial navigation guidance.

In some implementations, no curvilinear cannula is used to advance the tools 115 to create the defects 130. For example, a shape set memory metal alloy or polymer can be used that has a trocar tip for creating the endplate microfracture fenestration. In some implementations, the cannula and/or the drill shaft can be laser cut to reduce the strain associated with deforming the tubing or shaft or the instrument from its straight-wrought geometry.

In an implementation, the intervertebral disc space can be "splinted" or fixed by an intervertebral load transferring device or devices (e.g. interlaminar or interspinous process spacers or a pedicle screw fixation system). The postoperative splinting can be temporary (e.g. for three to eighteen months) load sharing to improve the intervertebral conditions for reparative healing, by reducing intervertebral disc loading following micro-fenestration. In some implementations, pedicle screws can be applied in a percutaneous or minimally-invasive manner for a period of time during which the disc space can heal under reduced mechanical demands. The pedicle screws can be cannulated and placed over guide pins that are inserted along the pedicle axis as described herein replacing or within the pedicle transport cannula 105. The pedicle screws can be subsequently dissociated from the connecting rod between them or completely removed once adequate healing is achieved to allow the disc to assume full mechanical loading. Healing can be assessed, for example, by imaging the disc, and/or with patient symptomology, and/or with a prescribed period of time.

As mentioned above, the non-linear (as well as linear) approaches described herein for therapeutically targeting the vertebral endplate can allow for the delivery of one or more therapeutic agents. The therapeutic agents can be delivered via cannulated (or cannulated and fenestrated) implants to the vertebral endplate and/or adjacent disc. In some implementations, a micro-tubule can be used to deliver high focal concentrations of an exocrine like drug and hormone through the devices described herein implanted via the non-linear transpedicular approach. The therapeutic can be solubilized or suspended therapeutic agent. The agent delivered in this way can result in a relatively low systemic effect.

In some implementations, a channel or series of channels can be created to or through the endplate and an implanted catheter(s) can be "threaded" within a non-linear channel cannula and subsequently connected to an implanted (i.e. intra-corporeal) subcutaneous port/reservoir. A fluid pump can optionally be implanted and connected to the reservoir. Polymer constructed catheter(s) can be secured to a threaded metal implant using a threaded ring and annular constricting collet means. Therapeutic agent(s) can then be injected via a hypodermic needle into the subcutaneous port into the catheter(s) and/or into the reservoir for delivery to the endplate, adjacent to the endplate, or through the endplate. Similarly, therapeutic agent(s) can be delivered through a linear cannulated or cannulated and fenestrated nail or screw that is positioned adjacent to or through the endplate.

The proposed "drug" delivery system can provide for the delivery of "orthobiologics", including analgesics, anaesthetics, antiinflamatants, growth factors, and other biologically active compounds (e.g. cytokine inhibitors, metalloproteinase inhibitors, c Jun NH(2)-terminal kinase (JNK)—inhibitors, interleukin-6 inhibitors, etc.) in high local concentrations and exceedingly low systemic concentrations. Potentially, growth factors that promote cartilage or bone production (e.g. BMP-2 or BMP-7) can be delivered to the intervertebral disc space to encourage disc healing or fusing the intervertebral disc space without implanting an interbody cage or interbody distractor (with or without concurrent use of cannulated pedicle screw fixation).

The methods, systems and devices described herein can also be used to treat other spinal diseases such as juvenile and adolescent idiopathic scoliosis. Current techniques include non-corrective bracing and limited intervertebral fusion with corrective instrumentation. Neither technique is particularly appealing, as the bracing is poorly tolerated by the adolescent population, and the corrective fusion procedure destroys youthful motion segments and stiffens the spine. Although bracing can be terminated at any time, its effects are primarily that of arresting further deformity progression rather than reducing deformity that might exist at the initiation of treatment. Micro-fenestrations of the vertebral endplate via non-linear drilling can be performed as described above in the ranges of 0.25 mm to 3 mm in diameter, as well as larger diameters (i.e. greater than 3 mm) to create osseous bridges across the vertebral growth plate to subsequently tether the vertebra on the concave side of the deformity in one or several vertebra.

In an implementation, growth mediators can be delivered to the respective concave and convex regions of the vertebral growth plate (i.e. ring "apophysis") of the affected vertebrae to correct growth of the deformed spine. In some implementations, stimulating growth mediators such as Insulin Like Growth Factor (e.g. IGF-1) can be delivered or inhibitory growth mediators such as Insulin Like Growth Factor Binding Protein (e.g. IGFBP) can be delivered. Using the devices and methods described herein, the therapy can be "titrated" to provide optimum patient response, and can be terminated at any time, with little or no subsequent anticipated adverse patient residual effects.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A method of minimizing a symptom and/or treating a pathology of intervertebral disc degeneration, the method comprising:
    introducing a first cannula through a vertebra along an axis of at least one pedicle of the vertebra from a generally posterior to a generally anterior direction, the first cannula coursing at a first trajectory through at least a portion of a vertebral body;
    inserting a second cannula within a lumen of the first cannula, wherein the second cannula is constrained to a relatively straight configuration within at least a portion of the first cannula and at least a portion of the second cannula assumes a nonlinear or curvilinear geometry away from a longitudinal axis of the first cannula when positioned distal to the first cannula within at least a portion of the vertebral body of the vertebra forming a curvilinear path;
    penetrating a vertebral endplate to enter into the intervertebral disc space thereby creating a first defect in the vertebral endplate of the vertebra at a first location; and
    repeating the introducing, the inserting, and the penetrating steps thereby creating a plurality of additional defects in the vertebral endplate at additional locations different from the first location.

2. The method of claim 1, further comprising rotating the second cannula along the pedicle axis to alter a plane within which the second cannula resides.

3. The method of claim 1, further comprising tensioning a pliable, distal end region of the second cannula using a steerable feature to deflect the distal end region away from the longitudinal axis of the first cannula.

4. The method of claim 3, wherein the distal end region deflects to take on a curvilinear shape.

5. The method of claim 3, wherein the distal end region comprises one or more slits forming a plurality of movable segments.

6. The method of claim 5, wherein the steerable feature includes a cable or wire coupled to the plurality of movable segments that is actuatable by a user.

7. The method of claim 3, further comprising positioning a guide pin within the at least one pedicle of the vertebra along the axis of the at least one pedicle; and placing the first cannula over the guide pin.

8. The method of claim 1, wherein penetrating the vertebral endplate comprises advancing a translatable flexible curvilinear bone penetrating instrument fabricated from a superelastic metal through the second cannula.

9. The method of claim 8, wherein the bone penetrating instrument comprises a microfenestrating trocar tip, a drill, a burr drill, a pick micro-fracturing drill, a fluted drill, or a laser.

10. The method of claim 1, further comprising advancing a tool through an inner lumen of the second cannula, the tool comprising a flexible, non-linear shaft and a distal tip.

11. The method of claim 10, further comprising forming the channel from the vertebral body through the vertebral endplate using the distal tip of the tool.

12. The method of claim 10, wherein the distal tip of the tool is a micro-fenestrating trocar tip, a drill, or a burr drill.

13. The method of claim 1, further comprising advancing a catheter through the second cannula.

14. The method of claim 13, further comprising delivering at least one diagnostic tool through the catheter, the at least one diagnostic tool comprising a pressure transducer or a radio-dense material.

15. The method of claim 13, further comprising delivering at least one therapeutic agent through the catheter, wherein the at least one therapeutic agent comprises one or more of analgesics, anaesthetics, anti-inflammatories, growth factors, cytokine inhibitors, metalloproteinase inhibitors, c Jun NH(2)-terminal kinase inhibitors, interleukin-6 inhibitors, Insulin Like Growth Factor (IGF-1), Insulin Like Growth Factor Binding Protein (IGFBP), BMP-2, or B.

16. The method of claim 1, wherein the first cannula is positioned percutaneously from a posterior extracorporeal position.

17. The method of claim 1, further comprising placing a pedicle screw above and below the plurality of additional defects in the vertebral endplate so as to provide intervertebral distraction during a healing phase for chondrogenesis.

18. The method of claim 1, wherein the first trajectory is the same as or different from additional trajectories formed during the repeating the introducing step to create the plurality of additional defects.

19. The method of claim 1, wherein the defect has a diameter of between 0.25 mm and 3 mm.

20. The method of claim 1, further comprising:
- stimulating bleeding and recruitment of cellular and humoral inflammatory cytokine production adjacent the defect;
- inducing neovascularization and fibrocartilaginous formation along the channel and the defect; and
- lessening feelings of pain.

* * * * *